United States Patent [19]

Frey

[11] Patent Number: 5,759,386
[45] Date of Patent: Jun. 2, 1998

[54] PROCESS FOR THIOETHERIFICATION AND SELECTIVE HYDROGENATION OF LIGHT HYDROCARBONS

[75] Inventor: Stanley J. Frey, Palatine, Ill.

[73] Assignee: UOP, Des Plaines, Ill.

[21] Appl. No.: 780,977

[22] Filed: Jan. 9, 1997

[51] Int. Cl.[6] .................... C10G 45/04; C10G 45/00; C07C 5/03; C07C 5/22

[52] U.S. Cl. .................. 208/217; 208/208 R; 208/209; 208/213; 208/216 R; 208/238; 585/250; 585/258; 585/259; 585/260; 585/276; 585/664; 585/670; 585/671

[58] Field of Search ........................ 208/238, 208 R, 208/209, 213, 217, 216 R; 585/250, 258, 254, 260, 276, 664, 670, 671

[56] References Cited

U.S. PATENT DOCUMENTS

| | | | |
|---|---|---|---|
| 3,919,341 | 11/1975 | Germanas et al. | 585/670 |
| 4,695,560 | 9/1987 | Gattuso et al. | 502/222 |
| 4,775,462 | 10/1988 | Imai et al. | 208/189 |
| 5,087,780 | 2/1992 | Arganbright | 585/259 |
| 5,463,134 | 10/1995 | Frey | 568/59 |

OTHER PUBLICATIONS

"Reduce the Cost of Producing TAME, AM-94-52" presented at the 1994 National Petroleum Refiners Association annual meeting held Mar. 20-22, 1994 at San Antonio, Texas.

"ABB Lummus Crest/CD Technology for Total and Selective Hydrogenation of Steam Cracker $C_4$ Streams" presented at the 1993 Dewitt Petrochemical Review at Houston, Texas on Mar. 23-25, 1993.

*Primary Examiner*—Glenn Caldarola
*Assistant Examiner*—Thuan D. Dang
*Attorney, Agent, or Firm*—Thomas K. McBride; John F. Spears, Jr.

[57] ABSTRACT

A light hydrocarbon stream, such as a $C_3$–$C_5$ stream recovered from an FCC unit, is catalytically treated for the selective hydrogenation of dienes and for the removal of mercaptans by thioetherification. The effluent of the reaction zone is fractionated to remove light ends and thioethers in a dual section fractionation zone, with the interconnection of the sections facilitating a reduction in capital and operating costs.

7 Claims, 1 Drawing Sheet

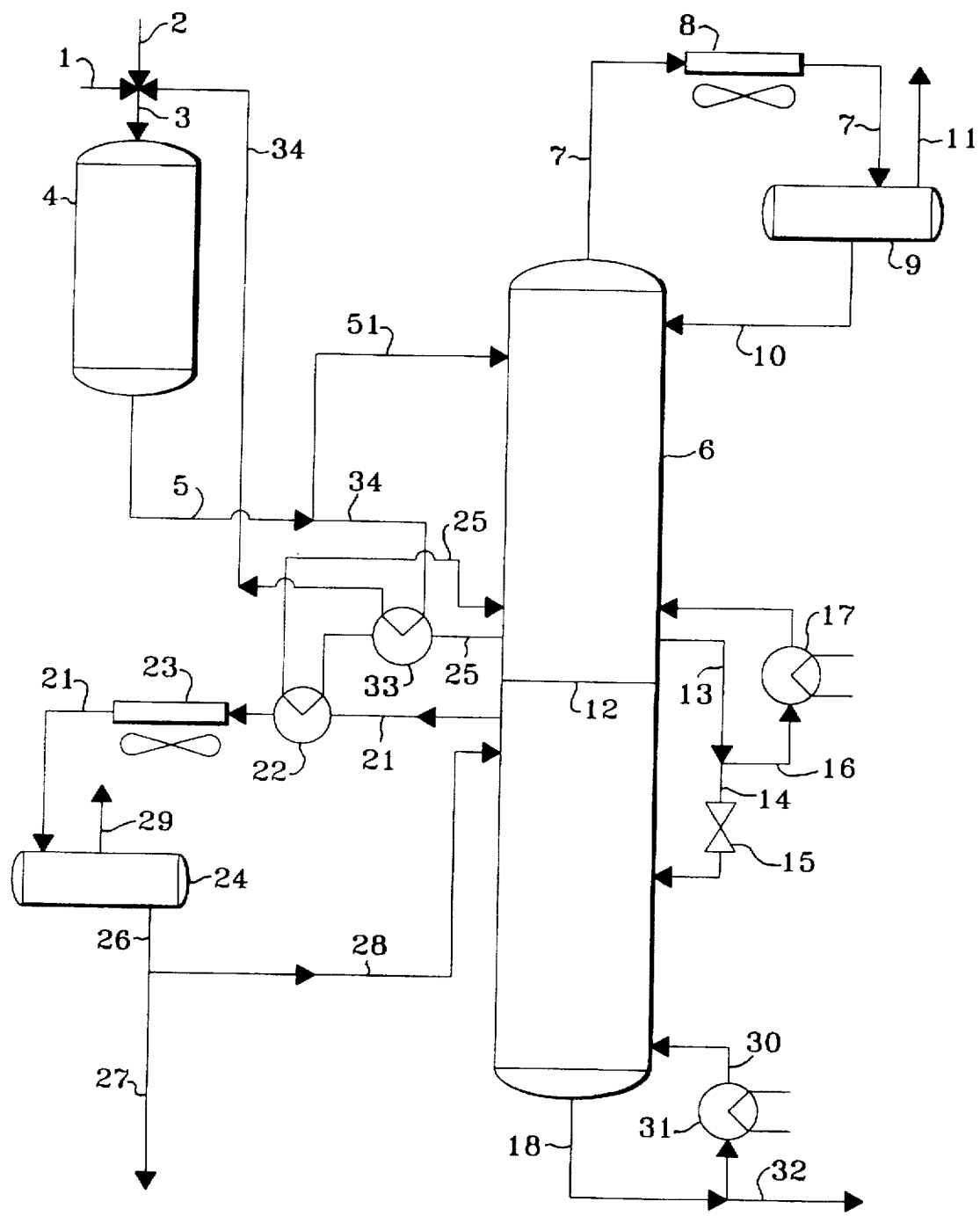

PROCESS FOR THIOETHERIFICATION AND SELECTIVE HYDROGENATION OF LIGHT HYDROCARBONS

BACKGROUND OF THE INVENTION

1. Field of the Invention

The invention relates to a hydrocarbon conversion process used to treat a light hydrocarbon feed stream to a downstream hydrocarbon conversion process. The invention specifically relates to a process for the simultaneous (one reactor) selective hydrogenation of dienes, non-skeletal isomerization of olefins, and removal of mercaptans from the feed stream to a motor fuel alkylation process.

2. Related Art

U.S. Pat. No. 4,775,462 issued to T. Imai et al. describes a process for the non-oxidative sweetening of a sour hydrocarbon fraction. This method is referred to herein as thioetherification and comprises contacting the sour hydrocarbon fraction with an acid catalyst in the presence of an unsaturated hydrocarbon at reaction conditions and converting the mercaptans to thioethers.

U.S. Pat. No. 5,463,134 issued to S. J. Frey describes a process for the performance of thioetherification in a catalytic distillation column along with the simultaneous thioetherification of olefinic hydrocarbons in the substantial absence of hydrogen.

A block diagram illustrating the multi-step treatment of a $C_5$-fraction derived from a light catalytic naphtha to prepare this stream for alkylation or thioetherification is shown as FIG. 2 in the paper entitled, "Reduce the Cost of Producing TAME, AM-94-52" presented at the 1994 National Petroleum Refiners Association annual meeting held March 20–22 at San Antonio, Tex. The process described in this paper also performs the selective hydrogenation of diolefins and the isomerization of linear butenes over a palladium catalyst. A process for the simultaneous selective hydrogenation of butadienes and the isomerization of butene-2 to butene-1 is described in U.S. Pat. No. 5,087,780 issued to R. T. Arganbright.

A paper entitled, "ABB Lummus Crest/CD Technology for Total and Selective Hydrogenation of Steam Cracker $C_4$ Streams" presented at the 1993 Dewitt Petrochemical Review at Houston, Tex. on Mar. 23–25, 1993 describes three separate but related process technologies for the hydrogenation of diolefins in a $C_4$ hydrocarbon stream derived from a steamcracker. This paper also addresses skeletal isomerization of normal butene to isobutene and feed preparation for alkylation units. The paper also addresses thioetherification for the removal of mercaptans from the feed stream.

BRIEF SUMMARY OF THE INVENTION

The invention is a hydrocarbon conversion process for the simultaneous conversion of mercaptans to higher boiling compounds, the isomerization of light mono olefins and the selective hydrogenation of diolefins. The invention is characterized in part by the unique integration of the fractional distillation equipment used to remove both the light materials such as hydrogen and the higher boiling sulfur-containing compounds from the effluent of the reaction zone. The cost of performing the fractional distillation is reduced by integrating reboilers and reducing the stripping and rerunning to a single column. This single column is often already available in a refinery as an existing stripper or depropanizer upstream of an acid catalyzed motor fuel alkylation unit, and the cost of installing the process is therefore minimized compared to a new unit or catalytic distillation in a new column.

One embodiment of the invention may be characterized as a hydrocarbon treating process which comprises the steps of combining a hydrogen feed stream, a recycle stream and a hydrocarbon feed stream to form a combined feed stream, which comprises propane, butane, hydrogen and methane, passing the combined feed stream through a reaction zone containing a bed of catalyst operated at conditions effective to simultaneously promote selective diene hydrogenation, the reaction of mercaptans and olefins present in the hydrocarbon feed stream to form thioethers and the isomerization of normal olefins and thereby forming a reaction zone effluent stream which comprises hydrogen, methane, propane, butane and thioethers; recovering heat from a first portion of the reaction zone effluent by indirect heat exchange against fluid removed from the stripping section of a unitary fractionation column, and then passing the first portion of the reaction zone effluent into the reaction zone as said recycle stream; passing a second portion of the reaction zone effluent into the stripping section of said unitary fractionation zone, which zone comprises an upper stripping section and a lower rerun section operated at differing reflux ratios, with the reflux ratio of the stripping section being greater than the reflux ratio of the rerun section; passing a liquid-phase process stream comprising butane and thioethers from the bottom of the stripping section into the rerun section; recovering a net overhead product stream, comprising hydrogen and ethane, from the stripping section and withdrawing the net overhead product stream from the process; recovering a liquid-phase butane-rich net product stream which is substantially free of thioethers by at least partially condensing a vapor phase process stream removed at the top of the rerun section, and withdrawing the net product stream from the process; and, recovering a net bottoms stream comprising thioethers from the bottom of the rerun section.

BRIEF DESCRIPTION OF THE DRAWING

The drawing is a simplified flow diagram showing a hydrocarbon feed stream of line 1 being processed in a reaction zone 4, with the effluent of the reaction zone being separated in an integrated fractional distillation zone 6.

DETAILED DESCRIPTION AND PREFERRED EMBODIMENTS

Many petrochemical and petroleum refining process units consume a feed stream comprising one or more light hydrocarbons such as propane, butane, butene or pentane. These feed streams originate in a number of different sources such as natural gas, dehydrogenation units and hydrocarbon conversion units. A common source of such $C_3$–$C_5$ light hydrocarbons is a fluidized catalytic cracking (FCC) unit in a petroleum refinery. The light hydrocarbons recovered from these sources normally contain a small amount of impurities including mercaptans derived from sulfurous compounds. The $C_3$–$C_5$ light hydrocarbons recovered, for example, from an FCC unit will also contain a mixture of various mono and diolefins. The mercaptans and diolefins, or dienes, are often considered to be contaminants which are detrimental to the performance of motor fuel alkylation units and other process units receiving the light hydrocarbon stream.

The mercaptans and the dienes in the feed stream can be removed by means of established commercial technology. For instance, the mercaptans can be removed by extraction using an aqueous caustic solution followed by oxidation of the mercaptans to disulfides as by the well known UOP Merox process. The dienes can be selectively hydrogenated to mono olefins. However, these are separate operations which each require their own physical equipment and entail separate operating expense. It is an objective of the subject invention to provide a process for treating light hydrocarbon streams which simultaneously removes both mercaptans and diolefinic hydrocarbons. It is another objective of the subject invention to provide a simplified process for removing light ends, mercaptans and diolefinic hydrocarbons from light hydrocarbon steams produced in an FCC unit.

The subject invention addresses three different feed pretreating areas encountered in the preparation of a light hydrocarbon chargestock for a hydrocarbon conversion process such as motor fuel alkylation. The invention addresses the removal of mercaptans from the feed stream, the reduction in the concentration of dienes such as butadiene, and the isomerization of mono olefins to a more desired isomer. In the prior art separate process units are employed for the mercaptan removal and hydrogenation steps, with the mono olefin isomerization possibly occurring simultaneously with the selective hydrogenation step. In the subject invention all three reactions are performed simultaneously in a single reaction zone, and then the desired product is recovered by separation of light impurities and heavy by-products by fractional distillation. By employing a single process unit to perform both the mercaptan removal and selective hydrogenation functions the subject invention lowers both the capital and operational costs of feed treatment.

It is a further objective of the subject invention to allow the effluent of this multi-function reaction zone to be fractionated and prepared for a downstream process unit in an existing fractionation column located upstream of the process unit. Specifically, the invention is intended to allow the effluent of the subject reaction zone to be fractionated in a stripping column now used to prepare the feed to a motor fuel alkylation zone.

The subject process will normally receive a feed stream which is derived from crude oil by fractionation, from natural gas by "condensate" separation, or from a hydrocarbon conversion step such as fluidized catalytic cracking, thermal cracking or hydrocracking. Each of these sources typically produces a feed which has been separated only on the basis of a range of boiling points or relative volatilities, and the feed will therefore contain a wide variety of different hydrocarbon compounds and impurities. The preferred feed stream is one which is rich in $C_4$ hydrocarbons, but the feed may also contain substantial amounts of $C_5$ hydrocarbons and be a blend rich in a mixture of $C_4$ and $C_5$ hydrocarbons. As used herein the term "rich" is intended to indicate a concentration of the indicated compound or class of compounds greater than 50 mole percent and preferably greater than 70 mole percent. Due to the inexact nature of separations performed using fractional distillation, the customary method of preparing the feed streams, the hydrocarbon feed stream will contain compounds other than the desired feed compounds. Hydrocarbons or other hydrocarbonaceous compounds such as mercaptans having boiling points close to those of the desired compounds will also be found to some extent in the feed stream. For instance, a small amount of $C_4$ hydrocarbons will normally be present in a "$C_5$ feed stream" and a small amount of propane will often be present in a butane stream. The hydrocarbon feed stream will normally contain sulfur compounds resulting in a sulfur concentration ranging from about 10 to about 350 wt ppm sulfur.

A second feed stream to the subject process is the hydrogen-rich gas stream which is passed into the reaction zone. This input stream is also a point of entry for compounds which are not desired in the feed to the downstream hydrocarbon conversion zone. The hydrogen feed stream to the process may comprise light hydrocarbons such as methane or ethane. Most of these light impurities will pass through the reaction zone without being converted.

The thioetherification reaction removes mercaptans from the feed stream by converting them to less volatile compounds which may then be readily separated from the feed stream by fractional distillation. The reaction joins the mercaptan to an olefin and produces a higher molecular weight thioether. This causes the effluent of the reaction zone to comprise the high boiling thioethers in addition to the light impurities mentioned above and the excess hydrogen unconsumed in the reaction zone.

Removal of both the light ends and the higher boiling sulfur compounds is desirable to prevent their entry into a downstream reaction zone and in particular to prevent their entry into an HF acid catalyzed motor fuel alkylation zone. Removal of both types of impurities would normally require a considerable amount of fractional distillation. For example, if the stripped and rerun product is to be taken out of a single conventional distillation column the sidecut point would have to be several trays below the feed point. Otherwise the product will contain light compounds. However, the sidecut must be taken off below the feed point in a single column, which requires that the sidecut be vapor phase if it is to contain a reduced amount of thioether. The vapor phase sidecut requirement greatly increases the heat duty in the column reboiler but more importantly it increases the required column diameter in the bottom of the column because the vapor flow from the bottom must supply the entire net product plus the required vapor traffic to effect good stripping and olefinic hydrocarbon recovery in the top portion of the column. The requirement of increased diameter will eliminate the possibility of using an existing column with a column diameter designed only for light ends stripping of an alkylation unit feed stream. This means that a new column would have to be built resulting in a substantial cost increase for the addition of the selective hydrogenation, isomerization and sulfur removal unit.

It is another objective of the subject process to provide a process for the performance of thioetherification and selective hydrogenation in a single reaction zone.

In the subject process the distillation zone is divided into two integrated sections or subzones. These two sections may be in physically separate columns located next to one another, but preferably are integrated into a single column and located one above the other as shown in the drawing. This preferred configuration greatly reduces the cost of the process over a two column system.

The drawing illustrates a preferred embodiment of the subject invention. In this embodiment a light hydrocarbon feedstream comprising a small amount of ethane due to imprecise fractional distillation but predominating in a mixture of $C_3$, $C_4$ and $C_5$ hydrocarbons enters the process by line 1 and is admixed with a hydrogen feed stream carried by line 2 and a recycle hydrocarbon stream carried by line 34. The result of the admixture of these streams is then passed into a fixed bed plug flow reaction zone 4 via line 3. This reaction zone contains a catalyst, as described herein, and is operated at conditions effective to promote the three desired reactions: thioetherification for mercaptan removal, butene isomerization and the selective hydrogenation of dienes. These reactions are performed at liquid phase conditions with the added hydrogen preferably not being sufficient to cause the formation of a separate vapor phase. The reactions which occur within zone 4 result in the effluent of the reaction zone having a composition which differs slightly from the combined feed to the reaction zone. The reaction zone effluent stream will contain thioethers resulting from the reaction of olefin hydrocarbons in the feed stream with mercaptan hydrocarbons also present in the feed stream. The reaction zone effluent stream will also have a reduced content of dienes compared to the hydrocarbon feed stream, and will have a higher concentration of butene-2 than the light hydrocarbon feed stream of line 1.

A first portion of effluent of the reaction zone 4 is diverted into line 34 and into heat exchanger 33. In this manner the required recycle stream of line 34 is cooled to remove the heat released in the reactions occurring in zone 4. This heat is recovered for use in the fractionation column by transfer into the bottom of the stripping section of fractionation column 6 via the fluid flowing in line 25. The fractionation zone 6 comprises an upper stripping section and a lower rerun section. For various economic and operational reasons these two sections are preferably interconnected as shown in the drawing, with the stripping section being physically located immediately above the rerun section. The remaining portion of the effluent of the reaction zone 4 is passed through line 51 into an intermediate point of the stripping zone of an integrated two section fractionation zone 6. This intermediate point is separated from each end of the stripping zone by vapor-liquid contacting media such as packing or two or more fractionation trays.

The function of the stripping zone is to remove light ends such as residual feed hydrogen and methane and ethane, which result from their presence in the hydrocarbon and hydrogen feed streams. These light materials and some small amount of the heavier hydrocarbons are removed as an overhead vapor stream through line 7 and passed through a condensing means 8. This results in the formation of condensate which is collected in the overhead receiver 9 and returned to the stripping section as reflux through line 10. Ethane and hydrogen are removed from the process as uncondensed vapor through line 11 at a rate controlled by a pressure control system not shown on the drawing.

Heat necessary to reboil the stripping section of the fractionation zone 6 is supplied by reboiling means 33, 22 and 17. Reboiler 33 recovers heat from the recycled portion of the reaction zone effluent to heat the fluid removed from the bottom of the stripping section via line 25. The reboiler 22 recovers heat from the lower rerun section of the fractionation zone 6 and partially vaporizes liquid to generate mixed-phase fluid returned to the stripping section. The reboiler 17 receives heat from an external source to heat and/or partially vaporize a portion of the bottoms liquid removed from the stripping section via line 13. This portion of the bottoms liquid is transferred via line 16 to the reboiler 17 and then returned to the stripping zone. In this manner almost 80% of the heat required to create the necessary vapor traffic is derived from the feed as it enters the column. This conserves the heat added to the reactor section feed stream and heat generated in the reactor.

The drawing has been simplified by the omission of certain normal and customary equipment required for the performance of fractional distillation and hydrocarbon processing. Therefore, such systems as control valves, control instrumentation and fractionation internals are not shown on the drawing. These items may be of customary design and do not form a part of the invention.

A liquid phase process stream is removed from the bottom of the stripping section through line 13 and divided into the portion carried by line 16 and passed into the reboiler 17 and a second portion passed through line 14 at a rate controlled by valve 15. This second portion is then routed to an intermediate point of the lower rerun section as the feed to the rerun section. The material flowing through line 14 is basically equivalent to the reaction zone effluent stream minus the light components removed by the stripping section. The feed to the rerun section should therefore be devoid of hydrogen and ethane and will contain substantially all of the $C_4$ and $C_5$ hydrocarbons, most of the $C_3$ hydrocarbons and the thioethers which were present in the reaction zone effluent stream of line 51. The fractional distillation performed in the rerun section drives the $C_3$, $C_4$ and $C_5$ hydrocarbons upwards as vapor, with these compounds being eventually removed from the top of the rerun section as a vapor phase stream through line 21. The rerun section overhead is then cooled by indirect heat exchange in the reboiler 22 and the cooler 23 before passage into the overhead receiver 24. The materials entering the overhead receiver 24 include a small amount of uncondensed vapor removed through line 29 as required through a pressure control system which may be linked to the overhead receiver 9. A stream of condensate is removed from the overhead receiver through line 26 and divided into a first portion returned to the rerun section by line 28 as reflux and a second portion removed from the process though line 27. The $C_3$, $C_4$ and $C_5$ hydrocarbons of line 27 represent the product of the subject process and may be passed into a downstream alkylation zone or other refining or petrochemical processing unit.

At the bottom of the rerun section a liquid stream is removed through line 18 and divided into a first portion passed through line 30 and a second portion which is removed from the process through line 32. The portion of the bottoms liquid removed through line 32 represents the net bottom product of the rerun section and will contain substantially all of the thioethers which enter the rerun section. The bottoms liquid flowing through line 31 passes through the indirect heat exchange reboiler 37 utilized to affect reboiling of the rerun section.

The composition of the catalyst used in the process is not part of the inventive concept and any suitable catalyst can be employed. Such a catalyst is expected to contain a Group VIII metal hydrogenation component supported on a refractory inorganic oxide support although it is contemplated that metal-containing resin catalysts could be employed instead of the preferred catalyst. The preferred inorganic oxide support material is alumina but other refractories such as titania or a suitable nonzeolitic molecular sieve could also be employed. The hydrogenation metal can be cobalt, nickel, iron, platinum, ruthenium or palladium. Nickel is the preferred hydrogenation metal. A preferred catalyst contains from about 15 to about 35 wt percent nickel, calculated as elemental nickel, on a spherical alumina support which has been formed by the oil-dropping method described in U.S. Pat. Nos. 3,096,295; 3,496,115; 3,887,492; 3,926,849, and 4,250,058. The noble metal catalysts suffer loss of activity at the high sulfur levels described herein and are not preferred under the mild liquid-phase reaction conditions of the reaction zone.

The reaction zone preferably comprises a fixed bed of the catalyst operated in a downflow mode at liquid phase conditions. The reactor is preferably operated at a liquid hourly space velocity (LHSV) of about 2 to about 10 and a pressure sufficient to maintain liquid phase conditions. A pressure in the range of about 2425 kPa to about 4136 kPa is suitable, with a pressure of about 2750 kPa to about 3450 kPa being preferred. A general range of operating temperatures extends from about 90° to about 145° C., with operations within the range of from 115° to 135° C. being preferred. Hydrogen is added at a rate at least equal to the stoichiometrically required amount for the selective saturation of the di and triolefinic hydrocarbons present in the feed stream. Preferably an excess of hydrogen is added, with hydrogen addition rates on the order of about 2 moles $H_2$ per mole of diene being representative.

As previously mentioned the column could take the form of two separate side by side columns instead of the single unitary column as depicted in the drawing. Those skilled in the art will recognize that there are many other areas of possible variation in the design of the fractionation zone ranging from different types of reboiling and condensing systems to different internal vapor-liquid contacting structures. For instance the fractionation zone may contain fractionation trays, structured packing or random packing or a combination of packing and trays. The fractionation zone can also, if desired, contain catalyst retained in a means to perform catalytic distillation. The preferred catalyst retaining structure is described in U.S. Pat. No. 5,073,236.

EXAMPLE

The following example is based upon calculations performed by an industry accepted process simulation software package programmed based upon known operations and data derived from actual pilot plant tests using the preferred catalyst to process the feed used in the Example. The composition of various streams in the process of the drawing is given in the Table 1 below with the line number of the drawing being used to identify the stream. The feed is passed into the reaction zone at a temperature of approximately 125° C. and a pressure of 4100 kPa. The reactor contains 13000 kg of the preferred nickel on alumina catalyst. The effluent of the reactor is a liquid phase stream having a temperature of about 135° C. and is passed into a stripping section containing 18 fractionation trays. The effluent of the reactor is passed onto the 11th tray from the bottom of the stripping section.

The stripping section is operated with an overhead temperature of approximately 42° C. and a pressure at top of the stripping section of about 1930 kPa. This section of the fractionation zone is operated at total reflux of all condensible hydrocarbons to the stripping section. The stripping section is reboiled through the addition of approximately 190 kW of heat via reboiler 17 and approximately 1600 kw of heat from the heat exchanger 22, with this latter heat being recovered from overhead vapor removed from the rerun section in line 21. Bottoms liquid is withdrawn from the stripping section via line 14 at a rate of about 33,100 kgm per hour, flowing onto the 6th tray from the bottom of the rerun section. The rerun section is run with an overhead vapor temperature of about 115° C. at a pressure of about 1930 kPa. The condensation of the overhead vapor of line 21 produces a condensate which is removed via line 27 at a rate of about 32880 kgm/hr. The remaining 3170 kgm/hr of this liquid flows back to the top of the rerun section as reflux liquid resulting in the rerun section being run at a reflux ratio of about $0.1^R/_D$. A bottoms liquid stream is removed via line 18 and divided into the first portion passing through the reboiler 31 wherein about 2960 kW is added to the fractionation zone and a second portion removed via line 32 at a rate of about 220 kgm/hr at a temperature of approximately 158° C.

TABLE 1

| | Line 1 | Line 2 | Line 51 | Line 11 | Line 27 | Line 32 |
|---|---|---|---|---|---|---|
| Hydrogen | | 60.1 | 25.8 | 25.8 | | |
| Methane | | 9.8 | 9.8 | 9.8 | | |
| Ethane | 1209. | | 1209. | 1178. | 31. | |
| Propylene | 14909. | | 14760. | 3167. | 11593. | 0.7 |
| Propane | 5038. | | 5194. | 613. | 4581. | 0.4 |
| 1,3 Butadiene | 421. | | 1.6 | | 1.6 | |
| Isobutylene | 4990. | | 4944. | 4.7 | 4935. | 4.1 |
| 1-Butene | 3709. | | 2604. | 2.0 | 2600 | 2.3 |
| 2-Butenes | 9121. | | 10417. | 3.0 | 10399 | 14.4 |
| Butanes | 10900. | | 11157. | 9.6 | 11138 | 9.4 |
| Isoprene | 55 | | 3.9 | | 3.8 | 0.1 |
| 1-Pentene | 1298 | | 984. | | 973 | 11.2 |
| C-2-Pentene | 1946. | | 1674. | | 1644 | 29.4 |
| T-2-Pentene | 3324. | | 3905. | | 3840 | 64.6 |
| 2-Me-1Butene | 2816. | | 765. | | 755 | 9.7 |
| 3-Me-1Butene | 509. | | 164. | | 163 | 0.9 |
| 2-Me-2Butene | 3943. | | 6358. | | 6238 | 121 |
| Isopentane | 12146. | | 12181. | | 12056 | 125 |
| N-Pentane | 1523. | | 1530. | | 1498 | 31.4 |
| Mercaptans | 44.3 | | | | | |
| Thioethers | 0 | 0 | 85.2 | | 8.6 | 76.6 |

A preferred embodiment of the invention may be characterized as a process which comprises the steps of passing hydrogen, a recycle stream and a feed stream, which comprises a mixture of hydrocarbons having from 3 to 5 carbon atoms per molecule including alkanes, alkenes and dienes, through a reaction zone containing a bed of solid catalyst operated at conditions effective to promote selective diene hydrogenation, the reaction of mercaptans and olefins to form thioethers and the isomerization of normal olefins and thereby forming a reaction zone effluent stream, which comprises hydrogen, ethane, propane, butane, and thioethers; recovering heat from a first portion of the reaction zone effluent stream by indirect heat exchange against fluid removed from the stripping section of a unitary fractionation column, and then passing the first portion of the reaction zone effluent stream into the reaction zone as said recycle stream; passing a second portion of the reaction zone effluent stream into the upper section of said unitary fractionation column comprising an upper stripping section and a lower rerun section operated at differing reflux ratios, with the reflux ratio of the stripping section being greater than the reflux ratio of the rerun section, and with the stripping section being located above the rerun section; removing a liquid-phase process stream comprising butane and thioethers from the bottom of the stripping section, passing a first portion of the liquid-phase process stream into the rerun section as the hydrocarbon input stream of the rerun section and passing a second portion of the liquid-phase process stream into a first reboiler of the stripping section; recovering a vapor-phase net overhead product stream, comprising hydrogen and ethane, from the stripping section; recovering heat from a vapor-phase process stream removed at the top of the rerun section and which is substantially free of thioethers by indirect heat exchange in a second reboiler against liquid from the stripping section; recovering a paraffin-rich $C_3$–$C_5$ liquid-phase product stream from the vapor-phase process stream and, recovering a net bottoms stream comprising thioethers from the bottom of the rerun section.

What is claimed:

1. A hydrocarbon treating process which comprises the steps:

(a) combining a hydrogen feed stream, a recycle stream and a hydrocarbon feed stream to form a combined feed stream, which comprises propane, butane, hydrogen and methane, passing the combined feed stream through a reaction zone containing a bed of catalyst operated at conditions effective to simultaneously promote selective diene hydrogenation, the reaction of mercaptans and olefins present in the hydrocarbon feed stream to form thioethers and the isomerization of normal olefins, and thereby forming a reaction zone effluent stream which comprises hydrogen, ethane, propane, butane and thioethers;

(b) recovering heat from a first portion of the reaction zone effluent by indirect heat exchange against fluid removed from the stripping section of a unitary fractionation column, and then passing the first portion of the reaction zone effluent into the reaction zone as said recycle stream.

(c) passing a second portion of the reaction zone effluent into the stripping section of said unitary fractionation zone, which zone comprises an upper stripping section and a lower rerun section operated at differing reflux ratios, with the reflux ratio of the stripping section being greater than the reflux ratio of the rerun section;

(d) passing a liquid-phase process stream comprising butane and thioethers from the bottom of the stripping section into the rerun section;

(e) recovering a net overhead product stream, comprising hydrogen and ethane, from the stripping section and withdrawing the net overhead product stream from the process;

(f) recovering a liquid-phase butane-rich net product stream which is substantially free of thioethers by at least partially condensing a vapor phase process stream removed at the top of the rerun section, and withdrawing the net product stream from the process; and, (g) recovering a net bottoms stream comprising thioethers from the bottom of the rerun section.

2. The process of claim 1 wherein heat is recovered in condensing the vapor-phase process stream removed at the top of the rerun section is employed in reboiling the stripping section.

3. A hydrocarbon treating process which comprises the steps:

(a) passing a hydrogen feed stream and a hydrocarbon feed stream, which comprises a butane, a pentane and ethane, through a reaction zone containing a bed of catalyst operated at conditions effective to promote selective diene hydrogenation, the reaction of mercaptans and olefins present in the hydrocarbon feed stream to form thioethers and the isomerization of normal olefins, and thereby forming a reaction zone effluent stream which comprises hydrogen, ethane, pentane, butane, and thioethers;

(b) passing the reaction zone effluent into the upper section of a fractionation zone comprising an upper stripping section and a lower rerun section operated at differing reflux ratios;

(c) passing a liquid-phase bottoms stream, comprising butane, pentane and thioethers from the bottom of the stripping section into the rerun section;

(d) recovering a net overhead product stream, comprising hydrogen and ethane, from the stripping section;

(e) recovering heat from a butane-rich vapor-phase process stream, which stream is removed from the fractionation zone at the top of the rerun section and substantially free of thioethers, by indirect heat exchange in a first reboiler against liquid present in the bottom of the stripping section;

(f) recovering a liquid-phase product stream from the vaporphase process stream and, (g) recovering a net bottoms stream comprising thioethers from the bottom of the rerun section.

4. The process of claim 3 wherein the catalyst comprises about 15 to about 35 wt percent nickel on a spherical support comprising alumina.

5. The process of claim 3 wherein the reflux ratio of the stripping section of the fractionation zone is greater than the reflux ratio of the rerun section.

6. A hydrocarbon treating process which comprises the steps:

(a) passing hydrogen, a recycle stream and a feed stream, which comprises a mixture of hydrocarbons having from 3 to 5 carbon atoms per molecule including alkanes, alkenes and dienes, through a reaction zone containing a bed of solid catalyst operated at conditions effective to promote selective diene hydrogenation, the reaction of mercaptans and olefins to form thioethers and the isomerization of normal olefins and thereby forming a reaction zone effluent stream, which comprises hydrogen, ethane, propane, butane, and thioethers;

(b) recovering heat from a first portion of the reaction zone effluent stream by indirect heat exchange against fluid removed from the stripping section of a unitary fractionation column, and then passing the first portion of the reaction zone effluent stream into the reaction zone as said recycle stream;

(c) passing a second portion of the reaction zone effluent stream into the upper section of said unitary fractionation column comprising an upper stripping section and a lower rerun section operated at differing reflux ratios, with the reflux ratio of the stripping section being greater than the reflux ratio of the rerun section, and with the stripping section being located above the rerun section;

(d) removing a liquid-phase process stream comprising butane and thioethers from the bottom of the stripping section, passing a first portion of the liquid-phase process stream into the rerun section as the hydrocarbon input stream of the rerun section and passing a second portion of the liquid-phase process stream into a first reboiler of the stripping section;

(e) recovering a vapor-phase net overhead product stream, comprising hydrogen and ethane, from the stripping section;

(f) recovering heat from a vapor-phase process stream removed at the top of the rerun section and which is substantially free of thioethers by indirect heat exchange in a second reboiler against liquid from the stripping section;

(g) recovering a paraffin-rich liquid-phase product stream from the vapor-phase process stream and, (h) recovering a net bottoms stream comprising thioethers from the bottom of the rerun section.

7. The process of claim 6, wherein the catalyst comprises about 15 to about 35 wt. percent nickel on a spherical support comprising alumina.

* * * * *